United States Patent [19]

England

[11] 3,962,279

[45] June 8, 1976

[54] SYNTHESIS OF PERFLUOROPYRUVYL FLUORIDE DIMER

[75] Inventor: David Charles England, Wilmington, Del.

[73] Assignee: E. I. Du Pont de Nemours and Company, Wilmington, Del.

[22] Filed: June 6, 1975

[21] Appl. No.: 584,381

[52] U.S. Cl. .................................................. 260/340.2
[51] Int. Cl.² ...................................... C07D 317/32
[58] Field of Search ................................. 260/340.2

[56] References Cited

UNITED STATES PATENTS 3,321,517   5/1967   Selman ........................... 260/340.2

*Primary Examiner*—Norma S. Milestone

[57] ABSTRACT

The dimer of perfluoropyruvyl fluoride can be made by reacting hexafluoropropene epoxide with dimethyl formamide.

4 Claims, No Drawings

SYNTHESIS OF PERFLUOROPYRUVYL FLUORIDE DIMER

BACKGROUND OF THE INVENTION

1. Field of the Invention

This invention relates to a novel process for the synthesis of perfluoropyruvyl fluoride dimer.

2. Description of the Prior Art

Perfluoropyruvyl fluoride dimer has previously been prepared from the reaction of hexafluoropropene epoxide (HFPO) with benzophenone or benzaldehyde. This mode of preparation is described in Selman U.S. Pat. No. 3,321,517. The preparation involves heating a mixture of benzophenone (or benzaldehyde) and hexafluoropropylene epoxide in an autoclave at elevated temperatures (100°–300°C) under autogenous pressure to yield the perfluoropyruvyl fluoride dimer:

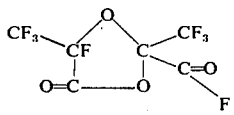

The quantities of materials are not critical as an excess of either reactant will merely remain unreacted.

The dimer is useful as a soil fumigant and insecticide and also as the intermediate for the synthesis of the monomer perfluoro-2-methylene-4-methyl-1,3-dioxolane (PMD). The latter, when polymerized, yields a clear polymer useful for making plastic contact lenses. The preparation of PMD from perfluoropyruvyl fluoride is described by Selman et al. U.S. Pat. No. 3,308,102, and its use in contact lenses, by Girard et al. U.S. Pat. No. 3,542,461.

SUMMARY AND DETAILED DESCRIPTION OF THE INVENTION

The present invention discloses the process for preparing the dimer of perfluoropyruvyl fluoride by reacting hexafluoropropene epoxide (HFPO) with dimethyl formamide (DMF) according to the equation:

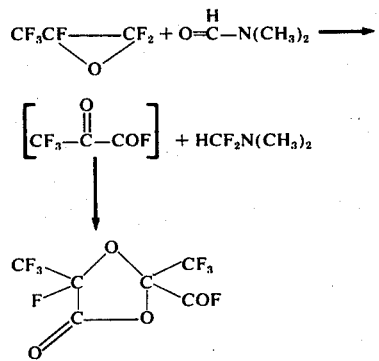

The reaction is readily carried out by contacting liquid dimethyl formamide with liquid or gaseous hexafluoropropene epoxide. The reaction temperature is not critical but will generally be between about 0° and 100°C. Pressure is likewise not critical but can readily be varied between about 0.1 and 5 atmospheres. Reaction time will, of course, depend on temperature and pressure but will generally be 5 to 30 minutes.

Contact between the reactants can be established and maintained in any convenient way, but the following procedures have been found useful:

1. Hexafluoropropene oxide gas is passed over dimethyl formamide in a flask fitted with a thermometer and gas inlet tube and the mixture maintained at about atmospheric pressure (740–760 mm Hg) to about 5 atmospheres and a temperature ranging from 0°–100°C: the higher the pressure employed, the lower the temperature used.

2. Liquid dimethyl formamide is poured into a Carius tube and frozen in a liquid nitrogen bath. The tube is then evacuated and hexafluoropropene epoxide added as a gas which quickly condenses to a liquid and then a solid on top of the DMF. The tube is then sealed, the contents melted, mixed and allowed to react with some evolution of heat. The Carius tube is cooled again with liquid nitrogen to open and the volatile material quickly distilled off under vacuum. The final product is obtained by redistillation at atmospheric pressure. There is no reaction when the liquids are too cold and at excessively high temperatures only a tarry product is obtained. The reaction accelerates at higher pressures. It is advantageous not to use pressure, however, as the reaction is rapid and exothermic below atmospheric pressure.

The following examples will serve to illustrate the practice of the invention:

EXAMPLE 1

Dimethyl formamide (14 g., 0.19 mole) was magnetically stirred in a flask fitted with a thermometer and gas inlet tube. The flask was flushed with HFPO gas and maintained automatically at about 740 mm. pressure of HFPO. Occasional cooling with an ice bath was necessary to keep the temperature just below 40°C. A total of 32 g. (0.10 mole) of HFPO was absorbed. More volatile products (33 g.) were quickly distilled into a liquid nitrogen-cooled trap under vacuum away from higher-boiling material (13 g.). Redistillation of material in the trap gave 11.5 g. (62.4%) of $HCF_2N(CH_3)_2$ and 14 g. (50.7%) of PPF dimer.

EXAMPLE 2

Liquid dimethyl formamide (14 g) and 36 g. of gaseous hexafluoropropene epoxide were separately condensed as solids and sealed under vacuum in a Carius tube (150 ml volume) at liquid nitrogen temperature. The mixture was allowed to warm to room temperature. On melting, the two materials were first immiscible and then mixed with some evolution of heat. The tube was cooled again in liquid nitrogen to open and volatile material quickly distilled under vacuum away from high-boilers. Redistillation at atmospheric pressure gave 9.9 g. (53.7%) of $HCF_2CON(CH_3)_2$, boiling mostly at 47°, and 16.8 g. (60.9%) of the dimer of perfluoropyruvyl fluoride, boiling mostly at 69°. The products were further characterized by comparison of their infrared spectra with those of the known compounds.

I claim:

1. The process of synthesizing the dimer of perfluoropyruvyl fluoride which comprises reacting liquid or gaseous hexafluoropropene epoxide with liquid dimethyl formamide.

2. The process of claim 1 wherein the temperature is between about 0° and 100°C and the pressure is between about 0.1 and 5 atmospheres.

3. The process of claim 1 wherein hexafluoropropene oxide gas is contacted with dimethyl formamide at a temperature of 0°–100°C and a pressure of up to about 5 atmospheres.

4. The process of claim 1 wherein the reactants are melted together from the solid state and then allowed to react together in the liquid state.

* * * * *